United States Patent [19]

Fuisz

[11] Patent Number: 5,501,858
[45] Date of Patent: Mar. 26, 1996

[54] RAPIDLY DISPERSABLE COMPOSITIONS CONTAINING POLYDEXTROSE

[75] Inventor: Richard C. Fuisz, Great Falls, Va.

[73] Assignee: Fuisz Technologies Ltd., Chantilly, Va.

[21] Appl. No.: 120,171

[22] Filed: Sep. 10, 1993

Related U.S. Application Data

[63] Continuation of Ser. No. 881,612, May 12, 1992, abandoned.

[51] Int. Cl.$^6$ .............................. A61K 7/00; A61K 47/00
[52] U.S. Cl. ...................... 424/439; 424/401; 424/78.03; 424/440
[58] Field of Search ................... 424/440, 78.03, 424/439, 401

[56] References Cited

U.S. PATENT DOCUMENTS

| | | | |
|---|---|---|---|
| 2,826,169 | 3/1958 | Le Veen | 54/79.4 |
| 2,918,404 | 12/1959 | Mende et al. | 514/683 |
| 3,019,745 | 2/1962 | Du Bois et al. | 425/9 |
| 3,036,532 | 5/1962 | Bowe | 425/9 |
| 3,067,743 | 12/1962 | Merton et al. | 424/431 |
| 3,070,045 | 12/1962 | Bowe | 425/9 |
| 3,073,262 | 1/1963 | Bowe | 425/9 |
| 3,095,258 | 6/1963 | Scott | 264/177.14 |
| 3,131,428 | 5/1964 | Mika | 264/177.13 |
| 3,308,221 | 3/1967 | Opfell | 264/174 |
| 3,324,061 | 6/1967 | Tanquary et al. | 264/211.17 |
| 3,557,717 | 1/1971 | Chivers | 107/54 |
| 3,595,675 | 7/1971 | Ash et al. | 99/130 |
| 3,615,671 | 10/1971 | Schoaf | 99/78 |
| 3,625,214 | 12/1971 | Higuchi | 128/260 |
| 3,686,000 | 8/1972 | Lawrence | 99/134 |
| 3,723,134 | 3/1973 | Chivers | 99/134 |
| 3,762,846 | 10/1973 | Chivers | 425/7 |
| 3,856,443 | 12/1974 | Salvi | 425/9 |
| 3,875,300 | 4/1975 | Homm et al. | 424/28 |
| 3,925,525 | 12/1975 | LaNieve | 264/40 |
| 3,930,043 | 12/1975 | Warning et al. | 426/515 |
| 3,951,821 | 4/1976 | Davidson | 252/1 |
| 3,967,623 | 7/1976 | Butterworth et al. | 128/287 |
| 3,992,265 | 11/1976 | Hansen | 195/127 |
| 4,090,920 | 5/1978 | Studer, Jr. | 195/127 |
| 4,136,145 | 1/1979 | Fuchs et al. | 264/164 |
| 4,153,512 | 5/1979 | Messner et al. | 195/103.5 |
| 4,293,570 | 10/1981 | Vadasz | 426/3 |
| 4,303,684 | 12/1981 | Pitchon et al. | 426/312 |
| 4,371,516 | 2/1983 | Gregory et al. | 424/22 |
| 4,376,743 | 3/1983 | Dees | 264/103 |
| 4,492,685 | 1/1985 | Keith et al. | 424/28 |
| 4,496,592 | 1/1985 | Kuwahara et al. | 426/5 |
| 4,500,546 | 2/1985 | Turbak et al. | 514/781 |
| 4,526,525 | 7/1985 | Oiso et al. | 425/9 |
| 4,585,797 | 4/1986 | Cioca | 514/773 |
| 4,619,833 | 10/1986 | Anderson | 426/548 |
| 4,793,782 | 12/1988 | Sullivan | 425/7 |
| 4,855,326 | 8/1989 | Fuisz | 514/53 |
| 4,873,085 | 10/1989 | Fuisz | 424/400 |
| 4,879,108 | 10/1989 | Yang et al. | 424/400 |
| 4,885,281 | 12/1989 | Hanstein et al. | 514/777 |
| 4,978,537 | 12/1990 | Song | 426/5 |
| 4,997,856 | 3/1991 | Fuisz | 514/777 |
| 5,011,532 | 4/1991 | Fuisz | 106/215 |
| 5,028,632 | 7/1991 | Fuisz | 514/772 |
| 5,034,421 | 7/1991 | Fuisz | 514/772 |
| 5,089,606 | 2/1992 | Cole et al. | 536/54 |
| 5,096,492 | 3/1992 | Fuisz | 106/215 |

FOREIGN PATENT DOCUMENTS

| | | |
|---|---|---|
| 88/2771 | 4/1988 | South Africa . |
| 88/2770 | 4/1988 | South Africa . |
| 89/9318 | 12/1989 | South Africa . |
| 90/2139 | 3/1990 | South Africa . |
| 90/8406 | 8/1991 | South Africa . |

*Primary Examiner*—Thurman K. Page
*Assistant Examiner*—Sally Gardner
*Attorney, Agent, or Firm*—Hoffmann & Baron

[57] ABSTRACT

Novel pharmaceutical and/or cosmetic compositions are disclosed containing a matrix prepared by melt-spinning polydextrose with one or more medicaments and/or cosmetic ingredients. Methods of preparing such compositions as well as treating various maladies are also disclosed.

35 Claims, No Drawings

RAPIDLY DISPERSABLE COMPOSITIONS CONTAINING POLYDEXTROSE

This is a continuation of application Ser. No. 07/881,612 filed on May 12, 1992 and now abandoned.

BACKGROUND OF THE INVENTION

The present invention relates to novel polydextrose-containing materials and to methods for preparing the same. In particular, the invention relates to readily dispersable polydextrose-containing medicaments or cosmetics.

In commonly-assigned U.S. Pat. Nos. 4,855,326 and 4,873,085, various active agents having pharmacological and/or cosmetic properties were combined with readily water-soluble melt-spinnable materials such as sugars or cellulosic substances. The active agents spun with these materials demonstrate enhanced solubility.

Commonly-assigned U.S. Pat. Nos. 5,011,532 and 5,096,492 contain examples of oleaginous substances that are mixed with sugar and melt-spun. The spun products disperse readily in water, forming colloidal or pseudo-colloidal dispersions. The '532 patent explains how oleaginous substances such as vegetable oil, mineral oil, baby oil, margarine, lanolin, cocoa butter and the like, which characteristically have little or no affinity for water, can have this characteristic altered by mixing the oleaginous substance with sugar and melt-spinning the mixture in a cotton candy spinning machine or equivalent. The disclosure of the '532 patent is incorporated herein by reference.

Other disclosures dealing with spinning substances with one or more sugars will be found in commonly-assigned U.S. Pat. Nos. 4,873,085; 4,997,856; 5,028,632 and 5,034,421. Generally, each of these disclosures are directed to melt-spinning sugar by introducing sugar and various ingredients into a cotton candy spinning machine. Such equipment is normally operated at a temperature of around 200° C. and at speeds of about 3,500 r.p.m. Melt-spinning in such equipment relies upon certain characteristics of sucrose, such as high crystallinity and high physical and chemical lability. The spun products disclosed in these patents are described as taking the form of a floss or mass of spun fibers.

Although the products discussed above are rapidly dispersable and even compactable, it has been desired to provide spun products in alternative forms which would facilitate handling of the spun product. In particular, it has been desired to provide the spun products in a form which is easier to work with, pour, and mix with other solids, etc. Such alternatives would provide higher efficiency for subsequent processing when the matrix is included in various goods or finished products.

Some efforts to alter the morphology of melt-spun products have centered around finding alternatives for sucrose. Attempts to spin non-sucrose or low-sucrose-containing saccharides have been, for the most part, unsuccessful. Feedstock having little or no sucrose as a carrier component were found to char during melt-spinning and were generally non-processable, especially on a commercial scale. It has been the belief of the artisan that sucrose is an important ingredient in feedstocks for melt-spinning processes.

Polydextrose is a non-sucrose, essentially non-nutritive carbohydrate substitute. Polydextrose can be prepared through polymerization of glucose in the presence of polycarboxylic acid catalysts and polyols. Generally, polydextrose is known to be commercially available in three forms: polydextrose A and polydextrose K, which are powdered solids, and polydextrose N supplied as a 70% solution. Each of these products also contain some low molecular weight components, such as glucose, sorbitol and certain oligomers.

In the past, most of the interest in polydextrose has centered around its use in various edible compositions. For example, polydextrose has stimulated interest in the food arts as a low-calorie bulking agent or as a part of many low-calorie or light foods since it has only about one-quarter of the calories of sucrose. Non-food related uses for the material have largely been ignored.

Unfortunately, the ability to disperse polydextrose and use it in different products has been limited by certain physical and chemical phenomena. Unlike most saccharide products, it is relatively unreactive and physically resistive to mixing and dispersing. While artisans have been able to process sugar to enhance its utility in food and other products, polydextrose heretofore did not appear to be as versatile.

The technical and processing difficulties alluded to above have therefore hampered the artisan's use of polydextrose and polydextrose-containing materials. If these difficulties could be overcome, especially in the areas of dipersability and solubility, the artisan would gain a useful non-sucrose alternative.

It is therefore an object of the invention to provide polydextrose-containing products having improved dispersability in liquids.

Other and further objects of the present invention are set forth in the following description, and its scope will be pointed out in the appended claims.

SUMMARY OF THE INVENTION

The present invention includes polydextrose-containing products prepared by melt-spinning a polydextrose feedstock containing one or more adjunct materials such as medicaments and/or cosmetics to provide a matrix. The polydextrose matrices of this invention are readily dispersable in solids and liquids. Readily dispersable means that the polydextrose matrix can be mixed with reduced mechanical mixing force when compared to polydextrose-containing feedstock which has not been melt-spun.

Numerous materials can be melt-spun with polydextrose conferring improved dispersion and solubility properties on the total product. These products have a wide variety of uses including pharmaceutical products, cosmetics and a variety of other products.

The present invention also includes novel processes for preparing a wide variety of melt-spun polydextrose-containing products. The products are prepared by admixing polydextrose and adjuvant materials to form a feedstock, melt-spinning the feedstock and recovering the product. Further processes include incorporating the melt-spun matrix with additional ingredients to produce pharmaceuticals, medicaments, cosmetics or the like. Moreover, methods of treatment are also included wherein the matrix is affixed to a site of treatment.

As a result of the present invention, a useful non-sucrose-containing matrix is provided. This alternative form allows bulking and dispersing properties beyond what sucrose-based matrices alone, usually in the form of floss and/or fibers, could provide. Thus, the versatile matrix can be readily used alone or in combination with other ingredients to form cosmetic or medicinal preparations, or, in other aspects, easily included as part of a topical lotion, ingestible liquid, tablet, capsule or the like.

The applications for these polydextrose-containing materials are vast. Consequently, pharmaceutical and cosmetic artisans have been equipped with a new tool which can be used to significantly enhance medicinal, cosmetic or even industrial systems especially when enhanced dispersability of a particular material in a useable medium is needed.

DETAILED DESCRIPTION OF THE INVENTION

The present invention is a composition and method utilizing polydextrose and one or more adjuvant materials to provide novel products. In particular, melt-spinning allows alteration of various physical, and in some cases, apparent chemical properties. Thus, polydextrose and products containing it can be altered with respect to solubility, wetability, and/or dispersability in aqueous and non-aqueous media. Moreover, the hydrophobic and/or lipophobic characteristics of polydextrose can be modified to provide the new products described herein, such as medicaments and/or cosmetics. In some aspects, the products of this invention can be used in lieu of freeze-dried materials.

The solid forms of polydextrose are in a form which is somewhat like powdered milk. As such, it can be difficult to disperse or dissolve. Vigorous stirring is required to incorporate it into water or aqueous liquids and it can lump or form difficult-to-disperse clumps of material, i.e., the "fisheye" phenomenon. In contrast thereto, the melt-spun polydextrose-containing products of the present invention enter into a dispersion in aqueous liquids with little or no mechanical agitation. Thus, the melt-spun polydextrose of the invention overcomes certain processing difficulties such as clumping and inability to flow in a dry state. Further, the novel polydextrose-containing compositions of this invention, in addition to enhanced dispersion properties, can be used to hold one or more ingredients combined in the matrix and release it over time.

As noted above, the products of this invention are prepared by a melt-spinning operation. One of the preferred methods for melt-spinning is through the use of apparatus such as those adapted to the production of cotton candy, or floss, from sugar. Illustrative of such machines is the Econo Floss Machine Model 3017 manufactured by Gold Medal Products Company of Cincinnati, Ohio. It will be appreciated by those skilled in the art from the present description that any apparatus or physical process which provides similar shear forces and time/temperature gradient conditions can also be used. For simplicity in disclosing and describing this invention, the term "melt-spinning" will be understood to mean a flash flow process which includes a combination of temperature, shear, flow, flow rate, mechanical forces and thermal gradients of the type used in a cotton candy-type machine. The apparatus is operated at a temperature and speed which permits flash flow but does not deteriorate the material undergoing the processing.

The flash flow process (or conditions comparable thereto) provides sufficient internal flow to permit transition in structure of the carrier material, herein polydextrose, without degradation of the carrier or any adjuvant material. Internal flow occurs when the infrastructure of the material breaks down sufficiently to permit movement of material at a subparticle level, and probably at a molecular level. At a molecular level, internal flow contemplates the movement of molecules relative to each other.

Internal flow of material is generally associated with the melting point or glass transition point. In this situation, however, it is contemplated that the combined application of heat and external force is sufficient to produce the flow at temperatures below the melting or glass transition point for most compositions.

An important benefit obtained by including polydextrose in the inventive matrix is that mixtures containing polydextrose can be spun at temperatures well below that of many other materials. For example, polydextrose has been successfully spun at temperatures of about 140° C., compared to temperatures of around 200° C. for sucrose. Polydextrose, therefore, provides the additional benefit of allowing lower processing temperatures in addition to short dwell times to allow a matrix to be formed before any degradation occurs.

An additional benefit associated with including polydextrose is that the resulting matrix can be in the form of a particle, flake, spicule or the like, conferring substantial advantages over sucrose-based forms such as a floss or spun fibers. These alternative morphologies allow subsequent processing and mixing to be more readily undertaken.

In one aspect of the invention, the adjuvant materials included with the polydextrose are medicament-related materials. Suitable categories of such ingredients may vary widely. Illustrative categories and specific examples include:

(a) Antitussives, such as dextromethorphan, and chlorphedianol hydrochloride;

(b) Antihistamines, such as chlorpheniramine maleate and terfenadine;

(c) Decongestants, such as phenylephrine, phenylpropanolamine, pseudoephedrine and ephedrine;

(d) Various alkaloids, such as codeine and morphine;

(e) Mineral supplements such as potassium chloride;

(f) Laxative, vitamins and antacids;

(g) Ion-exchange resins such as cholestyramine;

(h) Anti-cholesterolemic and anti-lipid agents;

(i) Antiarrhythmics such as N-acetyl-procainamide;

(j) Antipyretics and analgesics such as acetominophen, aspirin and ibuprofen;

(k) Appetite suppressants such as phenylpropanolamine hydrochloride or caffeine;

(l) Expectorants such as guaifenesin;

(m) Anti-anxiety agents such as diazepam; and (n) Anti-ulcer agents such as sucralfate.

A non-limiting list of other active ingredients includes anti-inflammatory substances, coronary dilators, cerebral dilators, peripheral vasodilators, anti-infectives, psychotropics, antimagics, stimulants, gastrointestinal agents, sedatives, antidiarrheal preparations, anti-anginal drugs, vasodilators, anti-hypertensive drugs, vasoconstrictors, migraine treatments, antibiotics, tranquilizers, antipsychotics, antitumor drugs, anticoagulants, antithrombotic drugs, hypnotics, anti-emetics, anti-nauseants, anticonvulsants, neuromuscular drugs, hyper- and hypoglycemic agents, thyroid and antithyroid preparations, diuretics antispasmodics, uterine relaxants, mineral and nutritional additives, antiobesity drugs, anabolic drugs, erythropoietic drugs, antiasthmatics, cough suppressants, mucolytics, anti-uricemic drugs, and mixtures thereof.

The medicaments contemplated herein are particularly well-suited for use when it is desired to disperse the agent in aqueous liquids and/or mask cover the undesirable tastes of actives. Generally, the medicament is mixed with polydextrose and melt-spun to obtain the medicament product. The flavor of unpleasant medicaments can also be masked or altered if desired by adding a flavoring agent and/or a sweetening agent to the pre-spun mixture.

In an alternative aspect of the invention, the adjuvant materials included with the polydextrose are cosmetic-related ingredients. Cosmetic ingredients are those materials which have a skin beautifying and/or complexion-related activity. Such products can be used externally on hair, skin or both. A non-limiting list of ingredients which have appearance-improving cosmetic activity includes dimethyl siloxanes, mucopolysaccharides, methyl and propyl parabens, biotin, lanolin, aloe, glycerin, mineral oil, nicotinamide compounds, sun screens, such as para-aminobenzoic acid, hair conditioners, moisturizers, moisturizing creams, astringents, powders such as talcs and combinations thereof.

In each of the above melt-spun aspects, the medicament or cosmetic ingredients can be included (1) within the matrix, (2) in addition to the matrix, or (3) both inside and outside the matrix.

It will be understood by those skilled in the art from the present description that additional materials can be included with the polydextrose and principle active ingredients. Thus, colors, dyes, pigments, antioxidants, preservatives and similar ingredients can be added in both the matrix and product in which the matrix is included. Such materials serve to improve the appearance, aroma, shelf-life or other properties of the products prepared and described herein. Moreover, the final products can also contain those adjuvant materials which are particularly suited for particular end uses.

The nature and amount of all materials included in the matrix will vary greatly. For example, it should be understood that polydextrose is spinnable by itself. Therefore, in general, the limit of polydextrose that can be included in any given composition has more to do with the desired morphology and nature of host matrix-carrier and guest activity. The amount of active material included in the matrix and/or product containing the matrix will depend upon the active and the amount required to achieve a desired therapeutic cosmetic effect. The exact amounts of the materials which make up the matrix and final products in which the matrix is included will therefore be within the level of ordinary skill of those in the art.

The matrix may further include an oleaginous substance added to the feedstock prior to processing. The oleaginous substance reduces dust blow-up which otherwise occurs during spinning of dry powders, however, the oleaginous substance is not necessary and the feedstock may be spun as a dry powder. A non-limiting list of oleaginous substances useful in the present invention is as follows: vegetable oils, corn oil, sunflower oil, olive oil, canola oil, and mixtures thereof.

In further aspects of the invention, supplemental materials such as bioadhesives, dispersants, surfactants and the like can be included in the matrix, products containing the matrix, or both. For example, bioadhesive-type materials such as hydrogels or synthetic materials such as polyvinylpyrrolidone are useful. Dispersants such as polyacrylates and alginates are also useful.

A non-limiting list of surfactants which are useful in combination with the matrix of the invention include as follows: anionic surfactants such as alkyl carboxylates, alkyl sulfates, ethoxylated alkyl sulfates, sulfosuccinate esters, isothionates, sarcosinates, sodium lauryl sulfoacetates, fatty acid-polypeptide condensates, linear alkyl arylsulfonates (LAS), alpha-olefin sulfonates (AOS), organic phosphate esters; cationic surfactants such as sodium lauryl sulfate (SLS), cetrimonium bromide and polysorbates; amphoteric surfactants such as alkylamino propionates, acyl ethylenediamines and betaines; non-ionic surfactants such as ethoxylated and propoxylated derivatives and polyol esters including sorbitan esters, polyoxyethylene ethers; alkyl polyglycosides, sulfonic acid/linear alkylate sulfonates, silicon derived phosphate esters, non-oxynol surfactans, TRITON™ brand surfactants and alkylphenols.

The invention also includes methods of treatment. The methods include contacting affected areas with the spun matrices containing medicaments such as described herein. The medicament-containing matrix can be placed in contact with the affected area in the as-spun form, as a compacted wafer or after being dispersed in a liquid. In the situations where the matrix is affixed directly to an affected area, non-exacerbating bioadhesive-type materials can also be included.

It will be understood from the present description that the dosages of any medicaments described herein can be varied depending upon the requirements of the patient, the severity of the condition being treated and similar considerations. The actual optimum dosage is within the skill of the artisan.

EXAMPLES

The following examples serve to provide further appreciation of the invention but are not meant in any way to restrict effective scope of the invention. Unless indicated otherwise, the Econo Floss machine referred to above was used to form the spun matrix. Operating temperatures were approximately 140°–150° C., spinning speed was approximately 3,500 r.p.m.

Example 1

| ACETOMINOPHEN-POLYDEXTROSE MATRIX | |
| --- | --- |
| INGREDIENTS | WEIGHT (GRAMS) |
| Acetominophen | 20 |
| Polydextrose K | 80 |
| Vegetable Oil | 40 |

In this Example, an acetominophen-containing matrix is prepared. All of the ingredients are thoroughly mixed and spun. A white spicule-like flake was obtained.

A tablespoon of the resulting flakes was contacted with water at room temperature. After quickly dissolving, a colloidal suspension was formed which had a viscosity thicker than that of the water alone.

A similar quantity of acetominophen, polydextrose and vegetable oil mixed together, but in non-spun condition, was placed in a container of water. The ingredients failed to disperse, leaving oil patches and clumps of dry materials.

Examples 2–3

The examples set forth below further exemplify the present invention.

| | WEIGHT (PERCENT) | |
| --- | --- | --- |
| INGREDIENTS | EX. 2 | EX. 3 |
| Acetominophen | 60.0 | 80.0 |
| Polydextrose | 30.0 | 15.0 |
| Corn Oil | 10.0 | 5.0 |
| | 100.0 | 100.0 |

In Examples 2 and 3, acetominophen melt-spun matrices were prepared. In each case, in spite of the low amount of polydextrose, the mixtures were melt-spun and provided light airy flakes. In each case, the flakes dispersed readily in water. The corn oil, even in amounts as low as 5%, was found to reduce the dust blow-up which otherwise occurs during spinning. It should be noted, however, that the presence of a vegetable oil is not necessary and that the ingredients could be spun as dry powders.

Example 4

ANTI-ULCER COMPOSITION

| INGREDIENTS | WT. (GRAMS) |
|---|---|
| Sucralfate (Powder) | 50.0 |
| Xanthan Gum | 10.0 |
| Corn Oil | 25 |
| Peppermint oil | 2 |
| Polydextrose-K | 438 |

In this Example, a sucralfate-containing anti-ulcer composition was prepared. Initially, the carrier material was prepared by mixing the xanthan gum, sucralfate, and polydextrose until a substantially homogeneous mixture was obtained. Thereafter, the corn oil and peppermint oil flavorant were added while mixing was continued. The resultant mixture was then spun at about 140° C. at 3600 r.p.m. A white spicule-like flake was obtained.

A one tablespoon quantity of the resulting matrix was added to a glass of tap water at room temperature. After quickly dissolving, a creamy yellow colloidal suspension was formed.

The resultant mixture was ingested by a host having distress from an ulcerated stomach. The inventive composition provided dramatic relief of stomach ulcer pain instantaneously. It appears that the unique combination of ingredients subjected to the high shear and heat processing had a remarkable effect on the speed and the extent of the treatment.

Example 5

ANTI-ULCER COMPOSITION

| INGREDIENTS | WT. (GRAMS) |
|---|---|
| Sucralfate (Powder) | 50 |
| Xanthan Gum | 10 |
| Corn Oil | 25 |
| Peppermint oil | 2 |
| Polydextrose-K | 438 |

In this Example, the medicament-containing matrix is prepared as in the Example 4. Fifteen grams of the flakes are added to a small amount of water to produce a viscous dispersion.

The dispersion was then placed on ulcer-bearing oral cavity tissue of an affected host. The hydrogel portion of the composition, xanthan gum, along with the medicament remain affixed to the oral cavity ulcer-bearing tissue to provide instantaneous relief from the discomfort associated with the ulcerated tissue in the oral cavity.

Example 6

| INGREDIENTS | WT. (GRAMS) |
|---|---|
| Cocoa Butter | 16 gr. |
| Samarkand Fragrance Oil | 16 gr. |
| Gleason Lite Mineral Oil | 16 gr. |
| Polydextrose-K | 160 gr. |
| Ethanol 95% | 3 gr. |

The ingredients were mixed together with a glass rod for about 10 minutes. This mixture was spun at about 140° C. at 3600 r.p.m. producing tan chips.

The tan chips were dissolved rapidly in tepid water producing a gorgeous colloidal bath water which is very comforting to the skin.

Example 7

| INGREDIENTS | WT. (GRAMS) |
|---|---|
| Dimethyl Polysiloxane | 10 gr. |
| Polydextrose-K | 90 gr. |

In this Example, the above ingredients were mixed by hand and then in a Cuisinart for four minutes. The mixture was spun at 140° C. at 3600 r.p.m. producing long silky chips.

The chips are then put in hot water resulting in a strong colloidal dispersion. The colloidal dispersion can be used in cosmetics to provide improved contact and adherence to the skin. Dimethyl Polysiloxane is a desired ingredient in many cosmetic and hair conditioner formulations but it is very difficult to form colloidal dispersions by conventional techniques.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

What is claimed is:

1. A pharmaceutical composition comprising a solid polydextrose-based matrix including a medicament, said matrix being readily dispersible in liquids to form a colloidal suspension, said composition formed by flash flow processing a medicament and a solid carrier comprising polydextrose, said carrier being resistive to dispersing prior to said flash flow processing.

2. The pharmaceutical composition of claim 1, wherein said medicament melt-spun with said polydextrose is selected from the group consisting of antitussives, antihistamines, decongestants, alkaloids, mineral supplements, laxatives, vitamins, antacids, ion exchange resins, anticholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, anti-diarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, anti-emetics, anti-nauseants, anti-convulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropaietic drugs, antiasthmatics, cough suppressants, mucolytics, anti-uricemic drugs and mixtures thereof.

3. The pharmaceutical composition of claim 1, further comprising an additional medicament.

4. The pharmaceutical composition of claim 3, wherein said additional medicament is selected from the group consisting of antitussives, antihistamines, decongestants, alkaloids, mineral supplements, laxatives, vitamins, antacids, ion exchange resins, anti-cholesterolemics anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psychotropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, antipsychotics, antitumor drugs, anticoagulants, antithrombotic drugs, hypnotics, anti-emetics, anti-nauseants, anticonvulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropaietic drugs, antiasthmatics, cough suppressants, mucolytics, anti-uricemic drugs and mixtures thereof.

5. The pharmaceutical composition of claim 1, wherein said matrix further comprises an oleaginous substance.

6. The composition of claim 5, wherein said oleaginous substance is selected from the group consisting of vegetable oils, corn oil, sunflower oil, olive oil, canola oil and mixtures thereof.

7. The composition of claim 6, wherein said oleaginous substance is present in an amount of from about 2 to about 20% by weight of said matrix.

8. The composition of claim 7, wherein said oleaginous substance is present in an amount of from about 5 to about 15% by weight of said matrix.

9. The composition of claim 1, wherein said matrix further comprises a member of the group consisting of surfactants, dispersing aids, adhesion promoters, flavors, sweeteners, dyes, preservatives and mixtures thereof.

10. The composition of claim 9, wherein said surfactants are selected from the group consisting of anionic surfactants, cationic surfactants, nonionic surfactants, amphoteric surfactants, alkylphenols and mixtures thereof.

11. The composition of claim 9, wherein said dispersing aids are selected from the group consisting of polyacrylates and alginates.

12. The composition of claim 9, wherein said adhesion promoter is a hydrogel.

13. The composition of claim 12, wherein said hydrogel is selected from the group consisting of xanthan gum, guar gum, carrageenan gum, gum tragacanth, alginates such as sodium alginate, gum karaya, locust bean gum, gum acacia and mixtures thereof.

14. The composition of claim 9, wherein said adhesion promoter is polyvinylpyrrolidone.

15. The composition of claim 1, further comprising a member of the group consisting of surfactants, dispersing aids, adhesion promoters, flavors, sweeteners, preservatives, dyes and mixtures thereof.

16. A method of preparing a solid pharmaceutical composition being readily dispersible in liquids to form a colloidal suspension comprising providing a mixture of a solid polydextrose-based matrix and a medicament, and flash flow processing said mixture to form said composition.

17. The method of claim 16, wherein said medicament melt-spun with said polydextrose is selected from the group consisting of antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-axiety agents, anti-ulcer agents, anti-inflammatory substances, coronary dilators, cerebral dilators, peripheral vasodilators, anti-infectives, psychotropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, antipsychotics, antitumor drugs, anticoagulants, antithrombotic drugs, hypnotics, anti-emetics, anti-nauseants, anticonvulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropaietic drugs, antiasthmatics, cough suppressants, mucolytics, anti-uricemic drugs, and mixtures thereof.

18. The method of claim 16, further comprising combining an additional medicament with said matrix.

19. The method of claim 18, wherein said additional medicament is selected from the group consisting of antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-axiety agents, anti-ulcer agents, anti-inflammatory substances, coronary dilators, cerebral dilators, peripheral vasodilators, anti-infectives, psychotropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, antipsychotics, antitumor drugs, anti-coagulants, antithrombotic drugs, hypnotics, anti-emetics, anti-nauseants, anticonvulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropaietic drugs, antiasthmatics, cough suppressants, mucolytics, anti-uricemic drugs, and mixtures thereof.

20. The method of claim 16, wherien said matrix further comprises an oleaginous material.

21. The method of claim 16, further comprising combining a member of the group consisting of surfactants, dispersing aids, adhesion promoters, flavors, dyes, sweeteners, preservatives and mixtures thereof with one of said matrix, said composition or said matrix and said composition.

22. A cosmetic composition comprising a solid polydextrose-based matrix including a cosmetic, said matrix being readily dispersible in liquids to form a colloidal suspension, said composition formed by flash flow processing a cosmetic ingredient with a solid carrier comprising polydextrose, said carrier being resistive to dispersing prior to said flash flow processing.

23. The cosmetic composition of claim 22, wherein said cosmetic ingredient is selected from the group consisting of dimethyl siloxanes, mucopolysaccharides, methyl and propyl parabens, biotin, lanolin, aloe, glycerin, mineral oil, nicotinamide compounds, sun screens, hair conditioners, moisturizers, moisturizing creams, astringents, powders and mixtures thereof.

24. The cosmetic composition of claim 22, further comprising an additional cosmetic ingredient.

25. The cosmetic composition of claim 24, wherein said additional cosmetic ingredient is selected from the group consisting of dimethyl siloxanes, mucopolysaccharides, methyl and propyl parabens, biotin, lanolin, aloe, glycerin, mineral oil, nicotinamide compounds, sun screens, hair conditioners, moisturizers, moisturizing creams, astringents, powders and mixtures thereof.

26. The cosmetic composition of claim 22, wherein said matrix further comprises an oleaginous substance.

27. The cosmetic composition of claim 26, wherein said oleaginous substance is selected from the group consisting of vegetable oils, corn oil, sunflower oil, olive oil, canola oil and mixtures thereof.

28. The cosmetic composition of claim 22, wherein said matrix further comprises a member of the group consisting of surfactants, dispersing aids, adhesion promoters, flavors, sweeteners, dyes, preservatives, and mixtures thereof.

29. The cosmetic composition of claim 22, which comprises dimethyl siloxane.

30. A method of preparing a cosmetic composition being readily dispersible in liquids to form a colloidal suspension comprising providing a mixture of a solid polydextrose-based matrix and a cosmetic, and flash flow processing said mixture to form said composition.

31. The method of claim 30, wherein said cosmetic ingredient is selected from the group consisting of dimethyl siloxanes, mucopolysaccharides, methyl and propyl parabens, biotin, lanolin, aloe, glycerin, mineral oil, nicotinamide compounds, sun screens, hair conditioners, moisturizers, moisturizing creams, astringents, powders and mixtures thereof.

32. The method of claim 30, further comprising an additional cosmetic ingredient.

33. The method of claim 32, wherein said additional cosmetic ingredient is selected from the group consisting of mucopolysaccharides, methyl and propyl parabens, biotin, lanolin, aloe, glycerin, mineral oil, nicotinamide compounds, sun screens, hair conditioners, moisturizers, moisturizing creams, astringents, powders and mixtures thereof.

34. The method of claim 30, wherein said matrix further comprises an oleaginous material.

35. The method of claim 30, further comprising combining a member of the group consisting of surfactants, dispersing aids, adhesion promoters, flavors, dyes, sweeteners, preservatives and mixtures thereof with one of said matrix, said composition or said matrix and said composition.

* * * * *